US009254205B2

(12) United States Patent
Wainwright et al.

(10) Patent No.: US 9,254,205 B2
(45) Date of Patent: Feb. 9, 2016

(54) VASCULAR STENT WITH IMPROVED VESSEL WALL APPOSITION

(71) Applicants: John Wainwright, Mission Viejo, CA (US); Michael Louis Losordo, San Juan Capistrano, CA (US)

(72) Inventors: John Wainwright, Mission Viejo, CA (US); Michael Louis Losordo, San Juan Capistrano, CA (US)

(73) Assignee: Covidien LP, Mansfield, MA (US)

(*) Notice: Subject to any disclaimer, the term of this patent is extended or adjusted under 35 U.S.C. 154(b) by 605 days.

(21) Appl. No.: 13/628,288

(22) Filed: Sep. 27, 2012

(65) Prior Publication Data

US 2014/0088678 A1    Mar. 27, 2014

(51) Int. Cl.
| | |
|---|---|
| *A61F 2/82* | (2013.01) |
| *A61F 2/86* | (2013.01) |
| *A61F 2/915* | (2013.01) |
| *A61F 2/962* | (2013.01) |
| *A61B 17/12* | (2006.01) |
| *A61F 2/95* | (2013.01) |

(52) U.S. Cl.
CPC .............. *A61F 2/86* (2013.01); *A61B 17/1214* (2013.01); *A61B 17/12118* (2013.01); *A61F 2/915* (2013.01); *A61F 2/962* (2013.01); *A61F 2002/823* (2013.01); *A61F 2002/91533* (2013.01); *A61F 2002/91558* (2013.01); *A61F 2002/9505* (2013.01); *A61F 2002/9534* (2013.01); *A61F 2230/0054* (2013.01); *A61F 2250/0071* (2013.01); *A61F 2250/0098* (2013.01)

(58) Field of Classification Search
CPC ............ A61F 2002/91558; A61F 2/82; A61F 2002/823; A61F 2002/91533; A61F 2002/9505; A61F 2230/0054; A61F 2/86

USPC ............................... 623/1.11, 1.15, 1.17–1.21
See application file for complete search history.

(56) References Cited

U.S. PATENT DOCUMENTS

| | | | |
|---|---|---|---|
| 5,800,520 | A | 9/1998 | Fogarty et al. |
| 6,129,755 | A | 10/2000 | Mathis et al. |
| 6,132,461 | A | 10/2000 | Thompson |
| 6,190,406 | B1 | 2/2001 | Duerig et al. |
| 6,235,053 | B1 | 5/2001 | Jang |
| 6,241,738 | B1 | 6/2001 | Dereume |
| 6,342,067 | B1 | 1/2002 | Mathis et al. |

(Continued)

FOREIGN PATENT DOCUMENTS

| | | |
|---|---|---|
| EP | 887051 A1 | 12/1998 |
| EP | 928606 A | 7/1999 |

(Continued)

*Primary Examiner* — Katherine M Shi
*Assistant Examiner* — Mohamed Gabr
(74) *Attorney, Agent, or Firm* — Mark J. Kertz, Esq.

(57) ABSTRACT

A medical device is provided that includes a vessel-engaging member attached to a distal end of a delivery wire. The vessel-engaging member includes a plurality of rows, with each row having a plurality of struts arranged in an alternating pattern such that for each row, a first set of vertices is positioned on a proximal side, and a second set of vertices is positioned on a distal side. The vessel-engaging member further includes a plurality of single bridges positioned between adjacent rows, each of the bridges connecting a vertex of a first row with a corresponding vertex of an adjacent second row. The vessel-engaging member can also include a plurality of double bridges positioned between adjacent rows, each of the double bridges connecting a vertex of a first row with two adjacent vertices of an adjacent second row.

38 Claims, 11 Drawing Sheets

(56) References Cited

U.S. PATENT DOCUMENTS

| | | |
|---|---|---|
| 6,524,337 B1 | 2/2003 | Bergeron |
| 6,533,808 B1 | 3/2003 | Thompson |
| 6,558,415 B2 | 5/2003 | Thompson |
| 6,673,106 B2 | 1/2004 | Mitelberg et al. |
| 6,764,507 B2 | 7/2004 | Shanley et al. |
| 6,818,013 B2 | 11/2004 | Mitelberg et al. |
| 6,884,260 B2 | 4/2005 | Kugler et al. |
| 6,939,371 B2 | 9/2005 | Kugler et al. |
| 7,300,458 B2 | 11/2007 | Henkes et al. |
| 7,309,351 B2 | 12/2007 | Escamilla et al. |
| 7,335,224 B2 | 2/2008 | Ohlenschlaeger |
| 7,442,203 B2 | 10/2008 | Ehr et al. |
| 7,556,644 B2 | 7/2009 | Burpee et al. |
| 7,618,445 B2 | 11/2009 | Moriuchi et al. |
| 7,632,300 B2 | 12/2009 | Thompson |
| 7,763,064 B2 | 7/2010 | Pinchasik |
| 7,803,180 B2 | 9/2010 | Burpee et al. |
| 7,896,912 B2 | 3/2011 | Shanley |
| 7,988,723 B2 | 8/2011 | Beach et al. |
| 7,993,383 B2 | 8/2011 | Hartley et al. |
| 8,007,528 B2 | 8/2011 | Yadin et al. |
| 8,048,146 B2 | 11/2011 | Young et al. |
| 8,066,757 B2 | 11/2011 | Ferrera et al. |
| 8,465,436 B2 | 6/2013 | Griswold |
| 8,500,794 B2 | 8/2013 | Beach et al. |
| 8,540,761 B2 | 9/2013 | Rabkin et al. |
| 8,540,763 B2 | 9/2013 | Jones et al. |
| 8,663,309 B2 | 3/2014 | Chobotov |
| 2002/0042647 A1 | 4/2002 | Jang |
| 2002/0128707 A1 | 9/2002 | Kavteladze et al. |
| 2002/0188341 A1 | 12/2002 | Elliott |
| 2002/0193862 A1 | 12/2002 | Mitelberg et al. |
| 2002/0198587 A1 | 12/2002 | Greenberg et al. |
| 2003/0176914 A1 | 9/2003 | Rabkin et al. |
| 2003/0187497 A1 | 10/2003 | Boylan et al. |
| 2003/0196717 A1 | 10/2003 | Nunez et al. |
| 2004/0015226 A1 | 1/2004 | Pelton |
| 2004/0015228 A1 | 1/2004 | Lombardi et al. |
| 2004/0034402 A1 | 2/2004 | Bales et al. |
| 2004/0039435 A1 | 2/2004 | Hancock et al. |
| 2004/0111147 A1* | 6/2004 | Rabkin et al. ............... 623/1.15 |
| 2004/0230291 A1* | 11/2004 | Richter ............... 623/1.15 |
| 2005/0080479 A1 | 4/2005 | Feng et al. |
| 2005/0125051 A1 | 6/2005 | Eidenschink et al. |
| 2005/0172471 A1 | 8/2005 | Vietmeier |
| 2005/0209678 A1 | 9/2005 | Henkes et al. |
| 2005/0261757 A1 | 11/2005 | Shanley |
| 2006/0155366 A1 | 7/2006 | LaDuca et al. |
| 2006/0190075 A1 | 8/2006 | Jordan et al. |
| 2006/0247759 A1 | 11/2006 | Burpee et al. |
| 2006/0247761 A1 | 11/2006 | Greenberg et al. |
| 2007/0203559 A1 | 8/2007 | Freudenthal et al. |
| 2007/0208416 A1 | 9/2007 | Burpee et al. |
| 2007/0276464 A1* | 11/2007 | Valencia et al. ............... 623/1.15 |
| 2007/0289677 A1 | 12/2007 | Ma et al. |
| 2008/0125855 A1 | 5/2008 | Henkes et al. |
| 2008/0294234 A1 | 11/2008 | Hartley et al. |
| 2009/0036976 A1 | 2/2009 | Beach et al. |
| 2009/0082846 A1 | 3/2009 | Chobotov |
| 2009/0216307 A1 | 8/2009 | Kaufmann et al. |
| 2009/0216308 A1 | 8/2009 | Hartley |
| 2009/0254165 A1 | 10/2009 | Tabor et al. |
| 2009/0326641 A1 | 12/2009 | Davis et al. |
| 2010/0004728 A1 | 1/2010 | Rao et al. |
| 2010/0286760 A1 | 11/2010 | Beach et al. |
| 2010/0292778 A1 | 11/2010 | Roeder et al. |
| 2011/0009940 A1 | 1/2011 | Grandfield et al. |
| 2011/0009941 A1 | 1/2011 | Grandfield et al. |
| 2011/0009950 A1 | 1/2011 | Grandfield et al. |
| 2011/0060212 A1 | 3/2011 | Slee et al. |
| 2011/0106234 A1 | 5/2011 | Grandt |
| 2011/0125252 A1 | 5/2011 | Goddard et al. |
| 2011/0230957 A1 | 9/2011 | Bonsignore et al. |
| 2012/0016463 A1 | 1/2012 | Ishida et al. |
| 2012/0083868 A1 | 4/2012 | Shrivastava et al. |
| 2012/0143237 A1 | 6/2012 | Cam et al. |
| 2012/0245671 A1 | 9/2012 | Wainwright et al. |
| 2012/0245672 A1 | 9/2012 | Arbefeuille et al. |

FOREIGN PATENT DOCUMENTS

| | | |
|---|---|---|
| EP | 1025812 A1 | 8/2000 |
| WO | WO-03/028588 A2 | 4/2003 |
| WO | WO-2006/044147 A2 | 4/2006 |
| WO | WO-2011/053693 A1 | 5/2011 |
| WO | WO-2011/144336 A1 | 11/2011 |

* cited by examiner

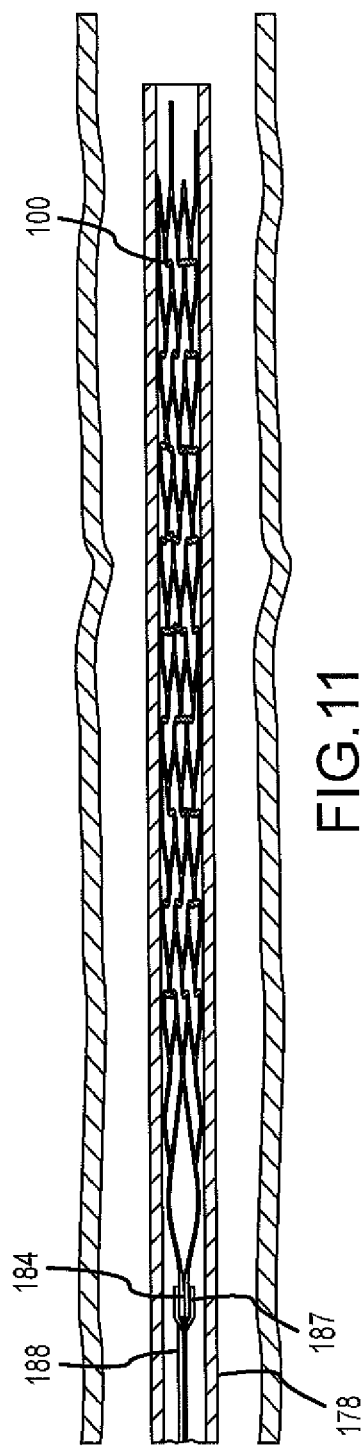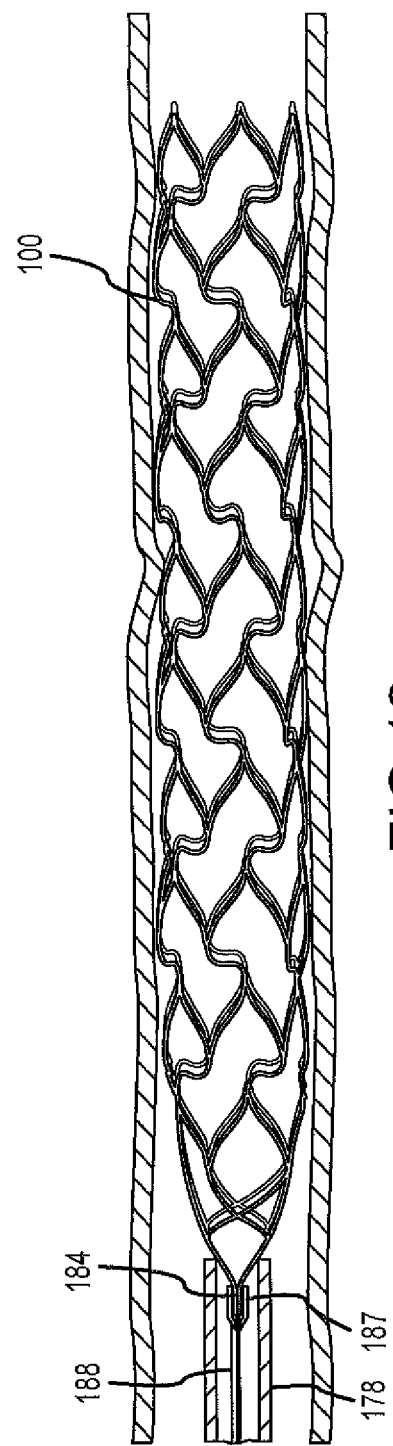
FIG. 11
FIG. 12

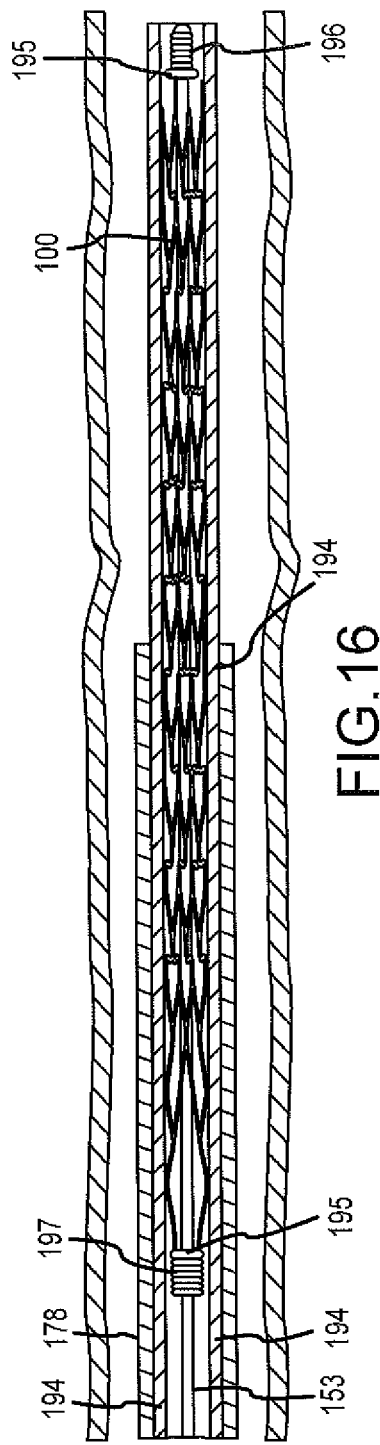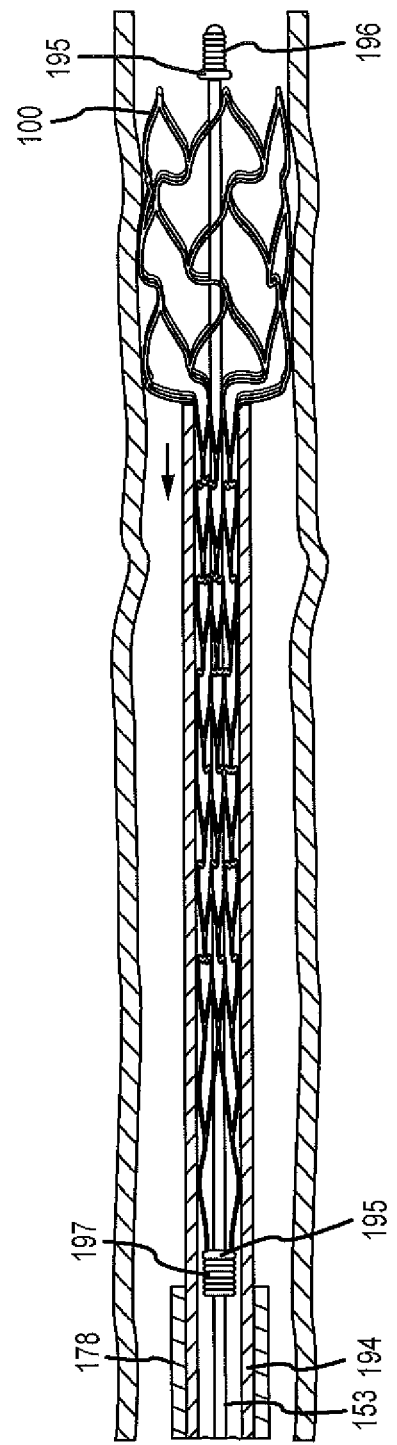

VASCULAR STENT WITH IMPROVED VESSEL WALL APPOSITION

BACKGROUND

Neurovascular (e.g., cerebral) aneurysms affect about 5% of the population. Aneurysms may be located, for example, along arterial side walls. The aneurysms may have a fundus, a neck, and a fundus-to-neck ratio or "neck ratio." If the neck ratio is greater than 2 to 1 or if the neck is less than 4 mm, the aneurysm may be treated with embolization coils alone because the coils will generally constrain themselves within the aneurysm without herniating into parent vessels. If the neck ratio is less than 2 to 1 or if the neck is greater than 4 mm, the aneurysms may be difficult to treat with embolization coils alone because the coils may be prone to herniating, or dislodging, into parent vessels. Dislodging of coils may cause arterial occlusion, stroke, and/or death.

In order to inhibit such dislodging, tubular neck remodeling devices may be used to keep coils or other materials within the fundus of the aneurysm and out of the vessels. Tubular remodeling devices generally consist of a braided wire or cut metallic stent or stents covering the neck of the aneurysm so that materials introduced into the fundus of the aneurysm do not herniate out of the aneurysm.

SUMMARY

The subject technology is illustrated, for example, according to various aspects described below. Various examples of aspects of the subject technology are described as numbered clauses (1, 2, 3, etc.) for convenience. These are provided as examples, and do not limit the subject technology. It is noted that any of the dependent clauses may be combined in any combination, and placed into a respective independent clause, e.g., clause 1, 20, 32, and 50. The other clauses can be presented in a similar manner.

1. A medical device, comprising:
   a delivery wire having a proximal end and a distal end; and
   a vessel-engaging member attached to the distal end of the delivery wire, the vessel-engaging member comprising:
   a plurality of rows, each row having a plurality of struts arranged in an alternating pattern such that for each row, a first set of vertices is positioned on a proximal side, and a second set of vertices is positioned on a distal side;
   a plurality of single bridges positioned between adjacent rows, each of the bridges connecting a vertex of a first row with a corresponding vertex of an adjacent second row; and
   a plurality of double bridges positioned between adjacent rows, each of the double bridges connecting a vertex of a first row with two adjacent vertices of an adjacent second row, wherein each of the plurality of double bridges is arranged generally along a line progressing laterally at an angle with respect to a longitudinal axis of the member.

2. The medical device of clause 1, wherein the first set of vertices are laterally offset from the second set of vertices.

3. The medical device of clause 1, wherein the plurality of single bridges positioned between a first row and an adjacent second row extend from the second set of vertices of the first row, downward to the first set of vertices of the second row, and wherein the plurality of single bridges positioned between the second row and an adjacent third row extends from the second set of vertices of the second row, upward to the first set of vertices of the third row.

4. The medical device of clause 1, wherein the plurality of double bridges are more rigid than the plurality of single bridges and thereby communicate a larger proportion of a longitudinal force than the plurality of single bridges.

5. The medical device of clause 1, wherein the plurality of single bridges comprises undulating members.

6. The medical device of clause 1, wherein the plurality of double bridges comprises undulating members.

7. The medical device of clause 1, wherein the single bridges positioned between a first row and an adjacent second row alternate laterally with the double bridges positioned between said adjacent rows.

8. The medical device of clause 7, wherein the alternating single and double bridges form a laterally-repeating pattern of two adjacent single bridges and one double bridge adjacent to one of the two adjacent single bridges.

9. The medical device of clause 8, wherein the single and double bridges positioned between the second row and an adjacent third row form the same laterally-repeating pattern as between the first row and the second row, wherein the double bridges between the second and third row are offset laterally from the double bridges between the first and second row.

10. The medical device of clause 8, wherein:
   the single and double bridges positioned between the second row and an adjacent third row form the same laterally-repeating pattern as between the first row and the second row;
   the single and double bridges positioned between the third row and an adjacent fourth row form the same laterally-repeating pattern as between the first row and the second row, and as between the second row and the third row;
   the double bridges between the second row and the third row are aligned laterally with the double bridges between the first row and the second row; and
   the double bridges between the third row and the fourth row are offset laterally from the double bridges between the first row and the second row, and from the double bridges between the second row and the third row.

11. The medical device of clause 10, wherein the pattern thus formed by the double bridges between the first row and the second row, the double bridges between the second row and the third row, and the double bridges between the third row and the fourth row, consisting of two longitudinally adjacent, laterally aligned sets of double bridges followed by one set of double bridges longitudinally adjacent to one of the two aligned sets and laterally offset therefrom, repeats along the length of the medical device.

12. The medical device of clause 10, wherein the double bridges between the third row and the fourth row are offset laterally from the double bridges between the first row and the second row, and from the double bridges between the second row and the third row, to the next lateral inter-vertex position on the distal vertices of the third row.

13. The medical device of clause 1, wherein the plurality of single bridges and the plurality of double bridges positioned between a first row and an adjacent second row are laterally offset from the plurality of single bridges and the plurality of double bridges positioned between the second row and an adjacent third row.

14. The medical device of clause 1, wherein an adjacent plurality of double bridges is positioned between the second row and a third row, the adjacent plurality of double bridges being longitudinally spaced from the plurality of double bridges.

15. The medical device of clause 1, further comprising first and second tapered sections, each of the tapered sections projecting from a proximal row and tapering in a direction from the proximal row toward the delivery wire.

16. The medical device of clause 15, wherein the first tapered section comprises a first and second connecting member with distal ends connected to the proximal row and proximal ends connected to the first tapered section.

17. The medical device of clause 16, wherein the first and second connecting members intersect.

18. The medical device of clause 15, wherein the first tapered section is connected to the proximal row at a middle vertex and a first strut endpoint, and the second tapered section is connected to the proximal row at the middle vertex and a second strut endpoint.

19. A medical device for insertion into a vessel, comprising:
   a frame comprising a plurality of rows, each row having a plurality of struts arranged in an alternating pattern such that for each row, a first set of vertices is positioned on a proximal side, and a second set of vertices is positioned on a distal side offset from the first set of vertices;
   a plurality of single bridges positioned between adjacent rows, each of the bridges connecting the second set of vertices of a first row with the first set of vertices of a second row; and
   a plurality of double bridges positioned between adjacent rows, each of the double bridges connecting a vertex of the first row with two vertices of the second row, wherein each of the plurality of double bridges is arranged generally along a line progressing laterally at an angle with respect to a longitudinal axis of the member.

20. The medical device of clause 19, wherein the first set of vertices are laterally offset from the second set of vertices.

21. The medical device of clause 19, wherein the plurality of single bridges positioned between a first row and an adjacent second row extend from the second set of vertices of the first row, downward to the first set of vertices of the second row, and wherein the plurality of single bridges positioned between the second row and an adjacent third row extends from the second set of vertices of the second row, upward to the first set of vertices of the third row.

22. The medical device of clause 19, wherein the plurality of double bridges are more rigid than the plurality of single bridges and thereby communicate a larger proportion of a longitudinal force than the plurality of single bridges.

23. The medical device of clause 19, wherein the plurality of single bridges comprises undulating members.

24. The medical device of clause 19, wherein the plurality of double bridges comprises undulating members.

25. The medical device of clause 19, wherein the single bridges positioned between a first row and an adjacent second row alternate laterally with the double bridges positioned between said adjacent rows.

26. The medical device of clause 25, wherein the alternating single and double bridges form a laterally-repeating pattern of two adjacent single bridges and one double bridge adjacent to one of the two adjacent single bridges.

27. The medical device of clause 26, wherein the single and double bridges positioned between the second row and an adjacent third row form the same laterally-repeating pattern as between the first row and the second row, wherein the double bridges between the second and third row are offset laterally from the double bridges between the first and second row.

28. The medical device of clause 26, wherein:
   the single and double bridges positioned between the second row and an adjacent third row form the same laterally-repeating pattern as between the first row and the second row;
   the single and double bridges positioned between the third row and an adjacent fourth row form the same laterally-repeating pattern as between the first row and the second row, and as between the second row and the third row;
   the double bridges between the second row and the third row are aligned laterally with the double bridges between the first row and the second row; and
   the double bridges between the third row and the fourth row are offset laterally from the double bridges between the first row and the second row, and from the double bridges between the second row and the third row.

29. The medical device of clause 28, wherein the pattern thus formed by the double bridges between the first row and the second row, the double bridges between the second row and the third row, and the double bridges between the third row and the fourth row, consisting of two longitudinally adjacent, laterally aligned sets of double bridges followed by one set of double bridges longitudinally adjacent to one of the two aligned sets and laterally offset therefrom, repeats along the length of the medical device.

30. The medical device of clause 28, wherein the double bridges between the third row and the fourth row are offset laterally from the double bridges between the first row and the second row, and from the double bridges between the second row and the third row, to the next lateral inter-vertex position on the distal vertices of the third row.

31. The medical device of clause 19, wherein the plurality of single bridges and the plurality of double bridges positioned between a first row and an adjacent second row are laterally offset from the plurality of single bridges and the plurality of double bridges positioned between the second row and an adjacent third row.

32. The medical device of clause 19, wherein an adjacent plurality of double bridges is positioned between the second row and a third row, the adjacent plurality of double bridges being longitudinally spaced from the plurality of double bridges.

33. The medical device of clause 19, further comprising first and second tapered sections, each of the tapered sections projecting from a proximal row and tapering in a direction from the proximal row toward the delivery wire.

34. The medical device of clause 33, wherein the first tapered section comprises a first and second connecting member with distal ends connected to the proximal row and proximal ends connected to the first tapered section.

35. The medical device of clause 34, wherein the first and second connecting members intersect.

36. The medical device of clause 33, wherein the first tapered section is connected to the proximal row at a middle vertex and a first strut endpoint, and the second tapered section is connected to the proximal row at the middle vertex and a second strut endpoint.

37. A method of implanting a medical device in a patient's neurovasculature comprising:
   inserting a guide catheter into the neurovasculature;
   advancing a microcatheter through a distal end of the guide catheter;
   advancing a vessel-engaging member through the microcatheter such that a distal portion of the member is located adjacent a treatment site in the neurovasculature, wherein the member comprises:

a plurality of rows, each row having a plurality of struts arranged in an alternating pattern such that for each row, a first set of vertices is positioned on a proximal side and a second set of vertices is positioned on a distal side;

a plurality of single bridges positioned between adjacent rows, each of the bridges connecting a vertex of a first row with a corresponding vertex of a second row; and a plurality of double bridges positioned between adjacent rows, each of the double bridges connecting a vertex of a first row with two adjacent vertices of an adjacent second row, wherein each of the plurality of double bridges is arranged generally along a line progressing laterally at an angle with respect to a longitudinal axis of the member; and withdrawing the microcatheter relative to the member to expose the member, the member being configured to expand against and engage the treatment site when unrestrained by the microcatheter.

38. The method of clause 37, wherein expanding against and engaging the treatment site comprises extending the vessel-engaging member across a neck of an aneurysm, wherein the vessel-engaging member inhibits dislodging of objects out of the neck of the aneurysm.

39. The method of clause 38, further comprising inserting embolic material into a fundus of the aneurysm.

40. The method of clause 38, wherein inserting embolic material comprises inserting coils.

41. The method of clause 37, further comprising detaching the vessel-engaging member via a connection mechanism.

42. The method of clause 41, wherein the connection mechanism comprises an electrolytically severable region.

43. The method of clause 41, wherein the electrolytically severable region comprises a member extending between first and second tapered sections, each of the tapered sections projecting from a proximal row of the vessel-engaging member and tapering in a direction from the proximal row toward a delivery wire attached to the vessel-engaging member.

44. The method of clause 41, wherein the connection mechanism comprises interlocking fingers disposed on a proximal end of the vessel-engaging member, the fingers configured to couple a delivery wire.

45. The method of clause 41, wherein the connection mechanism comprises a ball disposed at a distal end of a delivery wire and two paddles disposed on a proximal end of the vessel-engaging member, the paddles configured to couple the ball using a retractable sleeve that surrounds the paddles and the ball.

46. The method of clause 41, further comprising advancing longitudinally or distally the vessel-engaging member prior to detachment.

47. The method of clause 46, wherein the advancing comprises transmitting a majority of a longitudinal force from a pusher wire to a distal end of the member using the plurality of double bridges.

48. The method of clause 47, wherein the pusher wire is coupled to a proximal end of the vessel-engaging member.

49. The method of clause 46, wherein the advancing comprises transmitting a majority of a twisting force from a pusher wire to a distal end of the member using the plurality of double bridges.

50. The method of clause 37, wherein the treatment site is at a tortuous curve in an anatomical lumen.

51. A method of implanting a medical device in an anatomical lumen, the method comprising:

inserting a vessel-engaging member into the lumen, the member comprising:

a plurality of rows, each row having a plurality of struts arranged in an alternating pattern such that for each row, a first set of vertices is positioned on a proximal side and a second set of vertices is positioned on a distal side;

a plurality of single bridges positioned between adjacent rows, each of the bridges connecting a vertex of a first row with a corresponding vertex of a second row; and a plurality of double bridges positioned between adjacent rows, each of the double bridges connecting a vertex of a first row with two corresponding vertices of a second row, wherein each of the plurality of double bridges is arranged generally along a line progressing laterally at an angle with respect to a longitudinal axis of the member; and advancing the vessel-engaging member along the lumen by transmitting a majority of a longitudinal pushing force from a pusher, along the plurality of double bridges, to a distal portion of the member.

52. The method of clause 51, wherein the pusher is coupled to a proximal end of the vessel-engaging member.

53. The method of clause 51, wherein the advancing comprises transmitting a majority of a twisting force from a pusher, along the plurality of double bridges, to a distal portion of the member.

54. The method of clause 51, wherein the advancing comprises advancing the vessel-engaging member within a catheter in the lumen.

55. The method of clause 54, wherein the vessel-engaging member is advanced within the catheter while the vessel-engaging member is expanded against an inner wall of the catheter.

56. The method of clause 51, wherein the anatomical lumen comprises a tortuous curve.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

A detailed description will be made with reference to the accompanying drawings:

FIG. 11 depicts a partial cross section of a compressed medical device having a mechanically severable connection mechanism according to some embodiments of the subject technology.

FIG. 12 depicts a partial cross section of an expanded medical device having a mechanically severable connection mechanism according to some embodiments of the subject technology.

FIG. 16 depicts a partial cross section of a compressed medical device having a mechanically severable connection mechanism according to some embodiments of the subject technology.

FIG. 17 depicts a partial cross section of an expanded medical device having a mechanically severable connection mechanism according to some embodiments of the subject technology.

DETAILED DESCRIPTION

Figure 1A:
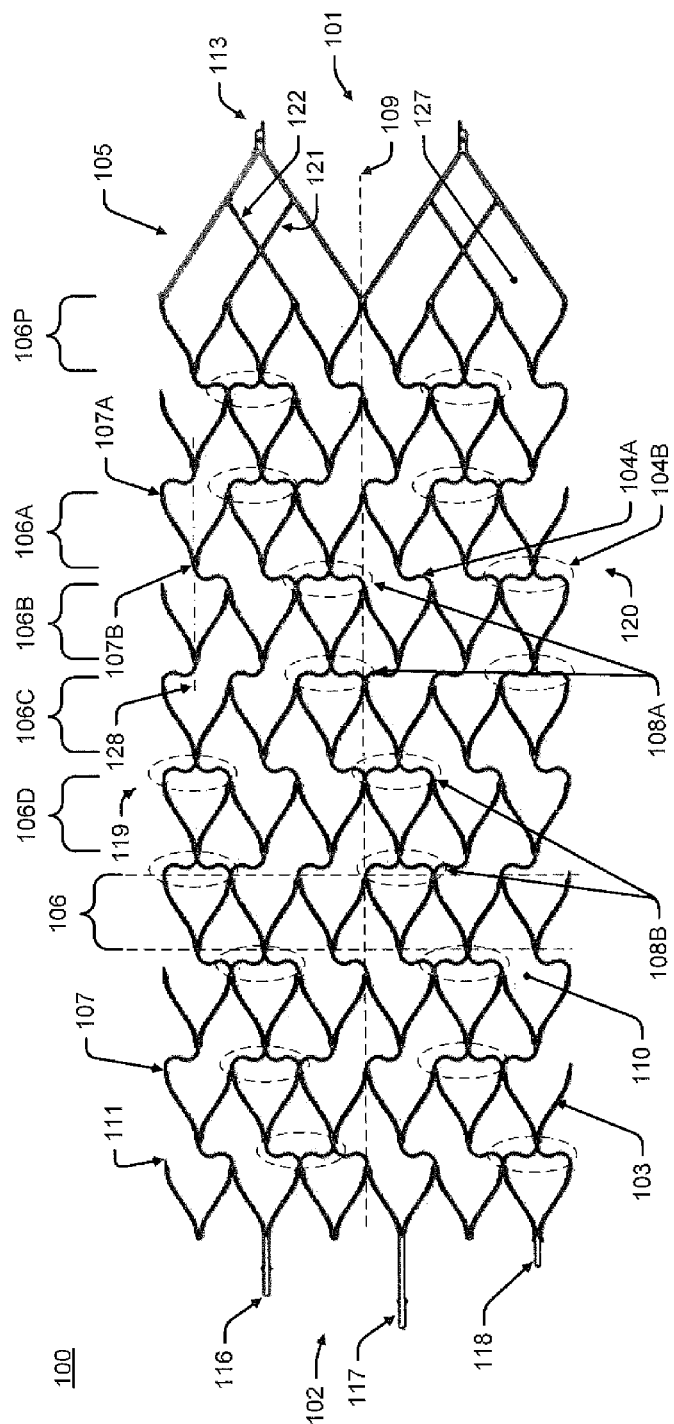
FIG. 1A depicts a medical device according to some embodiments of the subject technology.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology.

There have been numerous problems in the use of stents and vasoocclusive devices within the vasculature of the human body. Some devices ovalize when placed in a tortuous anatomical lumen. This may also be referred to as "kinking" or "fish mouthing." Other devices may herniate into an aneurysm. This problem may be referred to as "gator-backing", "I shelfing", and "ledge effect". Some devices abruptly move distally, or "jump," during the last portion of stent deployment. This may cause the proximal portion of the stent to protrude into the aneurysm also known as "ice cream cone" if the length is not oversized. Consequently, stents are often seen as having thrombogenic properties. Due to the need to use anticoagulants with such stents, few doctors have been known to be comfortable using such stents to treat a ruptured aneurysm. In some instances, an aneurysm may be ballooned and coiled, and then a stent is placed several weeks later to minimize the thrombogenic effect. Furthermore, visibility of stents under fluoroscopy is often difficult, and the trackability of stents in the vasculature has not been optimal.

The medical devices of the subject technology solves some or all of the foregoing problems by providing a vessel-engaging member designed for bridging a neck of an aneurysm that effectively prevents herniation or prolapse of objects (e.g., embolization coils, thrombi, etc.) out of the neck of the aneurysm. The vessel-engaging member may also allow the insertion of embolic material therethrough. The embolization coils may be a single embolization coil or other embolic material (e.g., embolic fluid).

The embolization coils or other embolic material may be inserted into a fundus of the aneurysm before or after positioning and deployment of the vessel-engaging member in an anatomical lumen or vessel. In some embodiments, the embolization coils are inserted in the fundus of the aneurysm using the same catheter from which the vessel-engaging member is deployed. In other embodiments, the embolization coils are inserted in the fundus of the aneurysm using a different catheter than the catheter from which the vessel-engaging member is deployed. In certain such embodiments, a guidewire may be used to guide both catheters.

The vessel-engaging member may engage a wall of the lumen utilizing various suitable means. For example, the vessel-engaging member may be a self-expanding stent and/or a balloon-expandable stent. In some embodiments, "vessel" or "lumen" may refer to blood vessels (including arteries and veins) or other suitable body organs having a lumen, such as the gastrointestinal tract (e.g., esophagus, stomach, small intestine, colon, rectum), bile ducts, urinary bladder, ureter, urethra, trachea, bronchi, and the like. As will be seen below, the medical device is designed such that a fully-deployed circumference of the vessel-engaging member more uniformly tracks an anatomical lumen, even in tortuous curvatures. The double bridge-strut configuration of the subject technology improves wall apposition, coil support, trackability, deployment accuracy, and radiopacity.

Figure 4:
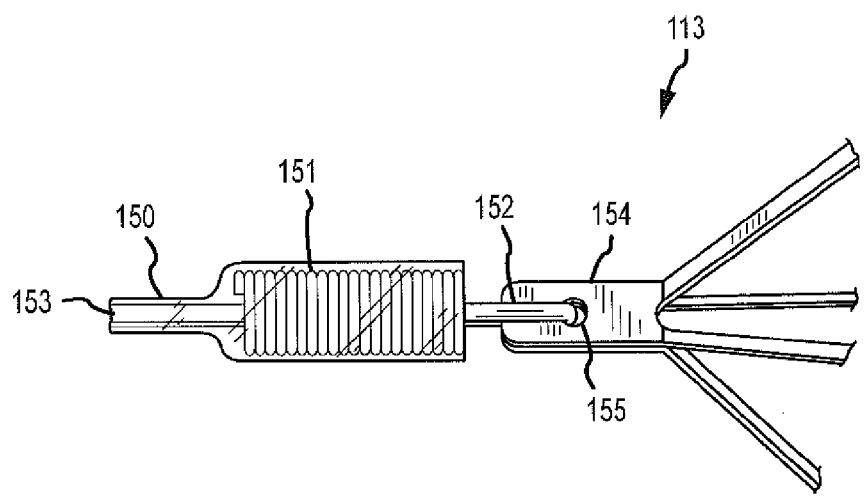
FIG. 4 depicts an electrolytically severable connection mechanism according to some embodiments of the subject technology.

FIG. 1A depicts a medical device including struts, single bridges, and double bridges, according to some embodiments of the subject technology. The medical device includes a delivery wire 153 (as shown in FIG. 4) having a proximal end and a distal end, and a frame or vessel-engaging member 100 attached to the distal end of the delivery wire 153. Referring to FIG. 1, the vessel-engaging member 100 includes a proximal end 101 and a distal end 102, and may be comprised of struts 103, single bridges 104A, and double bridges 104B. For example, the vessel-engaging member 100 may include a plurality of rows 106, with each row 106 having a plurality of struts 103 arranged in an alternating pattern such that for each row 106, a first set of vertices 107A is positioned on a proximal side, and a second set of vertices 107B is positioned on a distal side. The vessel-engaging member 100 may further include a plurality of single bridges 104A positioned between adjacent rows, with each of the single bridges 104A connecting a vertex 107 of a first row with a corresponding vertex 107 of an adjacent second row. The vessel-engaging member 100 may also include a plurality of double bridges 104B positioned between adjacent rows, with each of the double bridges 104B connecting a vertex 107 of a first row with two adjacent vertices 107 of an adjacent second row. The device may further include two tapered protrusions 105 at the proximal end 101 of the device for connecting the vessel-engaging member 100 to the delivery wire 153 (as shown in FIG. 4). In FIG. 1A, the vessel-engaging member 100 is shown cut longitudinally and laid flat.

The rows 106 of struts may be joined together at their vertices 107 by the plurality of single bridges 104A and the plurality of double bridges 104B. While nine rows 106 of struts 103 are illustrated in FIG. 1A, it is understood that any number greater than two rows of struts are suitable for the disclosure. As shown by FIG. 1A, the struts 103 of each row 106 may be alternatively positioned at a substantially 75 degree angle relative to each other in a zigzag-like pattern. Each vertex 107 (or bend point) is connected by a single bridge 104A or a double bridge 104B to a corresponding vertex or vertices of an adjacent row of struts.

As depicted by FIG. 1A, each row 106 may include twelve struts 103, each strut 103 alternating direction in a zigzag pattern. The strut length may, for example, range from about 1.50 millimeters (mm) to about 2.25 mm. Other strut lengths may be selected without departing from the scope of the technology. For example, the strut lengths may also be selected to be shorter to create more points to bend as the strut is flexed longitudinally and/or compressed or flexed at its diameter.

Figure 1B:
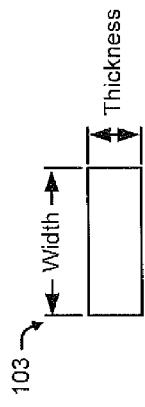
FIG. 1B depicts a perspective view of a strut according to some embodiments of the subject technology.
Figure 1C:
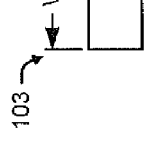
FIG. 1C depicts a cross-sectional view of a strut according to some embodiments of the subject technology.

FIG. 1B depicts a perspective view of a strut 103 according to some embodiments of the subject technology. FIG. 1C depicts a cross-sectional view of the strut 103 according to one aspect of the subject technology. As shown, the strut 103 has a rectangular cross-section. In some embodiments, a single bridge 104A or double bridge 104B may have a similar rectangular cross-section. However, the strut 103, the single bridge 104A, and the double bridge 104B, may have other suitable cross-sectional shapes, such as an elliptical cross-section (e.g., circular) or a polygonal cross-section.

In some embodiments, a strut width at the tip or vertex 107 of the strut 103 may be sized slightly larger than its width. For example, wherein a strut width of 0.055 is selected, a tip or vertex width of approximately 0.065 mm may be selected. The increased strength resulting from the increased width of the tips or vertices 107 may enhance durability of the medical device, for example, during deployment or retraction of the medical device from a deploying micro-catheter. In further aspects, one or more strut tip widths may be reduced to distribute strain on the medical device when deployed in certain tortuous configurations.

Referring to FIG. 1A, the plurality of single bridges 104A and the plurality of double bridges 104B may comprise undulating or straight members which extend in a generally lateral or radial direction. As used herein, a lateral direction is defined as a direction that is perpendicular to a longitudinal axis 109, and may be used to describe features of a flat pattern of the vessel-engaging member 100 as shown in FIG. 1A. In addition, as used herein, a radial direction is defined as a direction that is normal to the longitudinal axis 109 of the vessel-engaging member 100 that is along a radius of the vessel-engaging member 100. As described further below, a first edge 119 and a second edge 120 of the vessel-engaging member 100 may be connected to each other to form a substantially cylindrical shape by welding, soldering, or otherwise joining the strut tips 111 of the first edge 119 with the strut tips 111 of the second edge. Accordingly, a feature that is described as having a lateral characteristic in a flat pattern of the vessel-engaging member 100, may have a radial characteristic in a cylindrical shaped vessel-engaging member 100.

The single and double bridges, 104A and 104B respectively, may have a length ranging from about 1.5 mm to about 1.8 mm. As with strut lengths, the bridge length may be varied to be shorter or longer than the disclosed range without departing from the scope of the invention.

As depicted by FIG. 1A, the plurality of single bridges 104A and the plurality of double bridges 104B may be configured to maintain the first set of vertices 107A, of a row 106, substantially inline. In addition, the plurality of single bridges 104A and the plurality of double bridges 104B may be configured to maintain the second set of vertices 107B, of a row 106, substantially inline For a given row 106, the first set of vertices 107A may be laterally or radially offset from the second set of vertices 107B. For example, the distal vertices 107B may lay substantially along a line 128 that is parallel to the longitudinal axis 109 and the proximal vertices 107A may lay outside the line 128.

In some embodiments, each row 106 is mirrored and laterally shifted relative to an adjacent row, such that the vertices 107 connected by the plurality of single bridges 104A or the plurality of double bridges 104B are facing each other, inward, toward the bridges. Thus, while each bridge connects a mirrored vertex 107, the vertices of the rows 106 may appear to be oriented in the same direction. The configuration and arrangement of struts 103 and the plurality of single bridges 104A creates a matrix of cells 110 over the surface of the vessel-engaging member 100.

Referring to FIG. 1A, the single bridges 104A positioned between a first row 106A and an adjacent second row 106B may alternate laterally or radially with the double bridges 104B positioned between said first row 106A and second row 106B. For example, for a given row 106, the alternating single and double bridges, 104A and 104B respectively, may form a laterally-repeating pattern of two adjacent single bridges 104A and one double bridge 104B adjacent to one of the two adjacent single bridges 104A.

In some embodiments, the laterally-repeating pattern of the plurality of single bridges 104A and the plurality of double bridges 104B may repeat along two or more rows 106. For example, the single and double bridges positioned between the second row 106B and an adjacent third row 106C, may form the same laterally-repeating pattern as between the first row 106A and the second row 106B, described above. In addition, the single and double bridges positioned between the third row 106C and an adjacent fourth row 106D, may also form the same laterally-repeating pattern as between the first row 106A and the second row 106B, and as between the second row 106B and the third row 106C. In some embodiments, the double bridges positioned between the second row 106B and the third row 106C may be aligned laterally with the double bridges positioned between the first row 106A and the second row 106B. In other words, the plurality of double bridges 104B positioned between the second row 106B and the third row 106C may be longitudinally spaced from the plurality of double bridges 104B positioned between the first row 106A and the second row 106B.

In some embodiments, the double bridges positioned between the third row 106C and the fourth row 106D may be offset laterally or radially from the double bridges positioned between the first row 106A and the second row 106B, and from the double bridges positioned between the second row 106B and the third row 106C. The double bridges 104B positioned between the third row 106C and the fourth row 106D may be offset laterally or radially from the double bridges 104B positioned between the first row 106A and the second row 106B, and from the double bridges 104B positioned between the second row 106B and the third row 106C, to the next lateral inter-vertex position on the distal vertices 107B of the third row 106C.

As shown in FIG. 1A, the pattern thus formed by the double bridges 104B positioned between the first row 106A and the second row 106B, the double bridges 104B positioned between the second row 106B and the third row 106C, and the double bridges 104B positioned between the third row 106C and the fourth row 104D, may comprise two longitudinally adjacent, laterally aligned sets of double bridges 108A followed by one set of double bridges 108B longitudinally adjacent to one of the two aligned sets 108A and laterally offset therefrom.

In some embodiments, the pattern formed by the sets of double bridges 108A, 108B, may repeat along the length of the medical device. Each of the plurality of double bridges 104B may therefore, be arranged generally along one or more lines progressing laterally at an angle with respect to the longitudinal axis 109 of the vessel-engaging member 100. Although the sets of double bridges 108A, 108B depicted in FIG. 1A each include two double bridges 104B, it is understood that the sets of double bridges 108A, 108B may each include more than two double bridges 104B. Alternatively, it is also understood that the sets of double bridges 108A, 108B may each include only a single double bridge 104B.

Referring to FIG. 1A, the plurality of single bridges 104A positioned between the first row 106A and the adjacent second row 106B, may extend from the second set of vertices 107B of the first row 106A, downward to the first set of vertices 107A of the second row 106B. Downward, as used herein, refers to laterally or radially in one direction, while upward refers to laterally or radially in the opposite direction. The plurality of single bridges 104A positioned between the second row 106B and the adjacent third row 106C may extend from the second set of vertices 107B of the second row 106B, upward to the first set of vertices 107A of the third row 106C.

In some embodiments, the plurality of double bridges 104B are more rigid than the plurality of single bridges 104A. For example, because the double bridge 104B comprises two undulating members that connect a distal vertex 107B to two corresponding proximal vertices 107A, the double bridge 104B increases the rigidity of the vessel-engaging member 100. In contrast, the single bridge 104A comprises one undulating member that connects a distal vertex 107B to only one corresponding proximal vertex 107A. Accordingly, the double bridge 104B is more rigid than the single bridge 104A.

The plurality of double bridges 104B may communicate a majority or larger proportion of a longitudinal or twisting force than the plurality of single bridges 104A because the double bridges 104B are more rigid than the single bridges 104A. Generally, a load or force may be transmitted through the vessel-engaging member via the struts 103, the single bridges 104A, and the double bridges 104B. Because the double bridges 104B comprise two undulating members, compared to the single undulating member of the single bridge 104A, the double bridge 104B may communicate a larger proportion of the longitudinal or twisting force than adjacent single bridges 104A. Accordingly, the double bridges 104B transmit a majority of the longitudinal or twisting force from a pusher or delivery wire to the distal end 102 of the vessel-engaging member 100. Although the single and double bridges 104A, 104B are depicted as undulating members in FIG. 1A, it is understood that the single and/or double bridges 104A, 104B may comprise straight members. For the purposes of this disclosure, the subject technology may use a delivery wire and/or a pusher wire without limitation. In this regard, the term delivery wire may refer to what one skilled in the art may call a pusher wire and vice versa. Therefore, for simplicity, the terms delivery wire and pusher wire are used interchangeably.

In some embodiments, the single or double bridges, 104A and 104B respectively, may be thinner in width relative to the struts 103. For example, a strut width may range from about 0.055 mm to about 0.065 mm to provide sufficient radial support when the vessel-engaging member 100 is deployed in the anatomical lumen. In contrast, a width of the single or double bridges, 104A and 104B respectively, may range from about 0.045 mm to about 0.055 mm. Accordingly, the subject technology may include a thinner bridge width to enhance longitudinal flexibility, and provide better arching capability. When deployed in a tortuous anatomical lumen, the vessel-engaging member 100 will be more likely to bend at a single or double bridge, 104A and 104B respectively, location than at a strut 103 location, thus providing improved wall apposition at a curve.

The medical device may be implanted in a patient's neurovasculature by first inserting a guide catheter into the neurovasculature, then advancing a microcatheter through a distal end of the guide catheter, and then advancing the vessel-engaging member 100 through the microcatheter such that the distal portion 102 of the vessel-engaging member 100 is located adjacent a treatment site in the neurovasculature. After withdrawing the microcatheter relative to the vessel-engaging member 100 to expose and allow the vessel-engaging member 100 to expand against and engage the treatment site, the single bridges 104A and/or the double bridges 104B may bend and/or deflect to thereby allow the struts 103 to conform to the tortuous curvature of the lumen.

Figure 18:
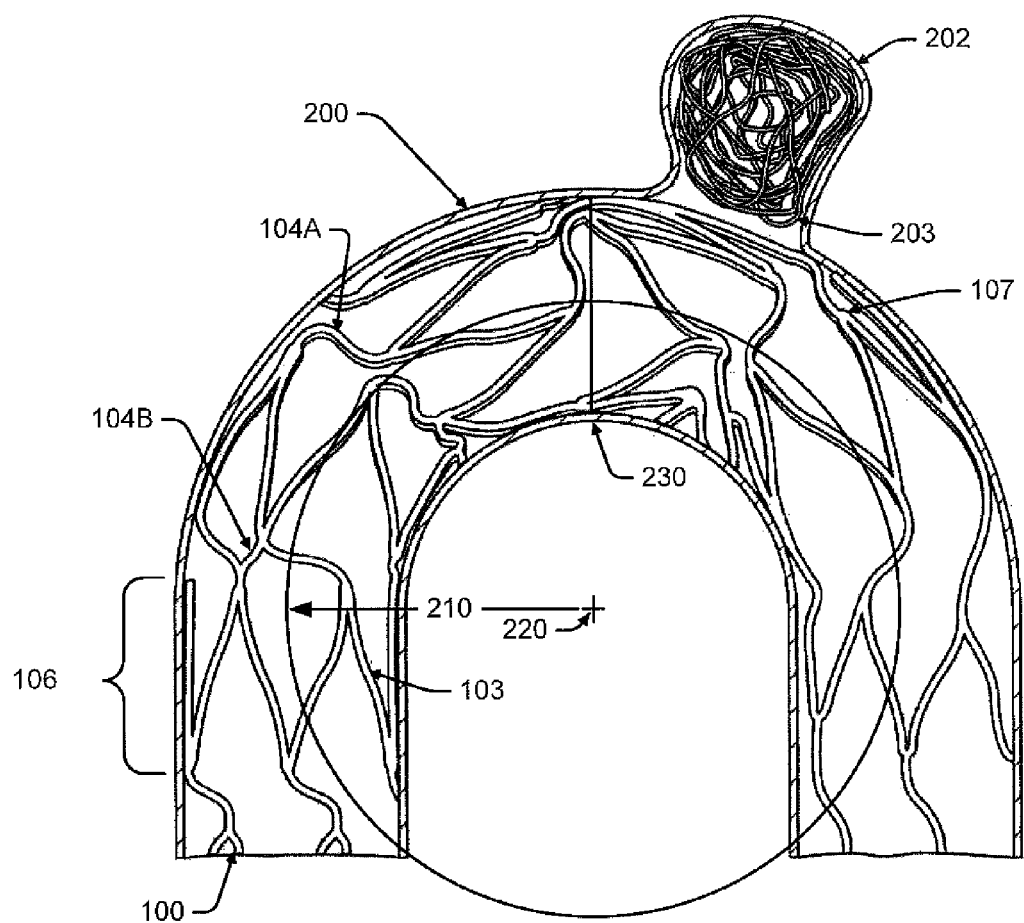
FIG. 18 illustrates a side view of a medical device in a tortuous lumen according to some embodiments of the subject technology.

For example, referring to FIG. 18, the lumen 200 may have a diameter of about 3 mm and may include a curve with a center point 220, having a radius 210 of about 3.9 mm. The curve may have an apex 230 located at a midpoint of the curve. The apex may also represent a peak of the curve, or a point on the curve equidistant from endpoints of the curve. At the apex 230, the single or double bridges, 104A and 104B respectively, adjacent the apex 230 are deflected to allow the vertices 107 adjacent to the deflecting bridges to contact an inner surface of the vessel or lumen, thereby providing improved wall apposition near the apex 230. In some embodiments, a distance between strut rows 106 disposed adjacent to the deflecting bridges is less than a distance between strut rows disposed away from the deflecting bridges. The reduced distance between the strut rows may cause the vertices 107 adjacent to the apex 230 to be near each other. In some embodiments, by allowing the vertices 107 to move near each other, the vertices 107 may better conform to the shape of the curve.

Because the vessel-engaging member 100 may better conform to the shape of the curve, the vessel-engaging member 100 is capable of effectively extending across a neck of an aneurysm 202 to inhibit dislodging of objects 203 out of the neck of the aneurysm 202.

Tapered Sections

As depicted by FIG. 1A, the device may also include one or more tapered sections 105 projecting from a proximal row 106P of struts and tapering in a direction from the proximal row 106P toward the delivery wire 153 (shown in FIG. 4). In some embodiments, the struts of the proximal (and/or distal) row may be selected to be longer than the struts of other rows 106. The proximal row 106P may be used for connecting the primary, workable structure of the medical device to the one or more tapered sections 105. For example, referring to FIG. 1A, each tapered section 105 may extend from four vertices 107 of the proximal row 106P, with each tapered section sharing an intermediate-positioned vertex. Each tapered section 105 may include a V shaped structure extending from the outer most end points (strut tips 111), and an X shaped structure within and supporting the V shaped structure, extending from the inner most vertices of proximal row 106P. For example, a first and second connecting member, 121 and 122 respectively, may extend from the inner most vertices of the proximal row 106P to the tapered section 105. The first and second connecting members, 121 and 122 respectively, may intersect thereby forming the X. The proximal end point of each tapered section (vertex of the V shaped structure) may further include a connection point 113 for detachable connection to a delivery wire, as discussed further below. Each delivery wire connection point 113 (and/or vertex of the V shaped structure) may be constructed from a radiopaque material or include a radiopaque marker allowing in vivo imaging of the stent.

Figure 2:
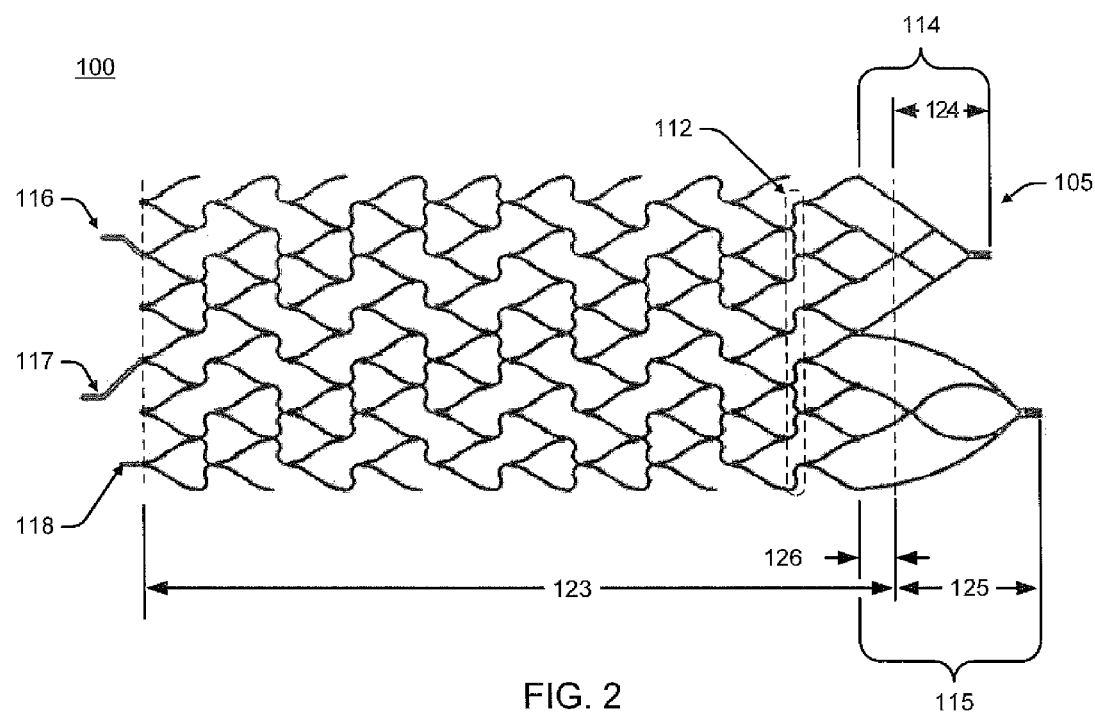
FIG. 2 depicts a flat pattern of a medical device according to some embodiments of the subject technology.
Figure 3:
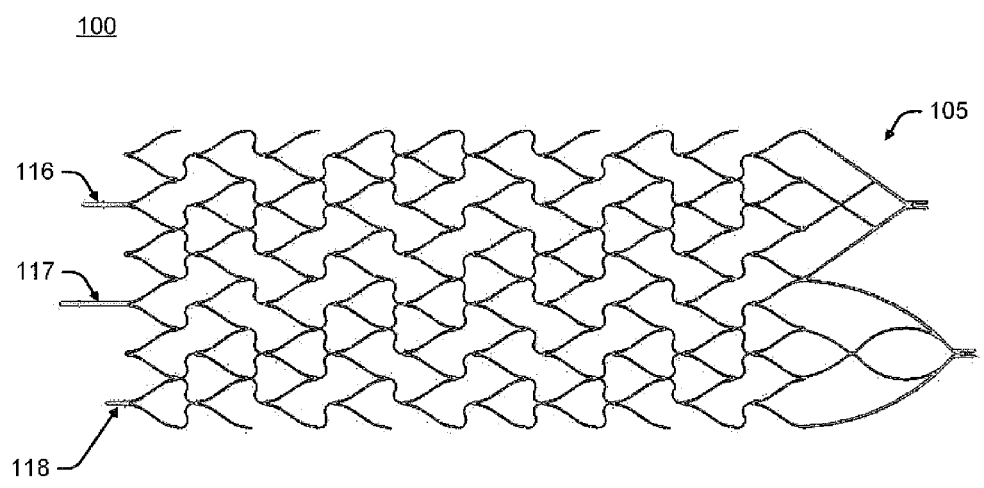
FIG. 3 depicts a flat pattern of a medical device according to some embodiments of the subject technology.

Each tapered section 105 may have a length measured along the longitudinal axis. As shown in FIG. 1A, the tapered sections 105 may have a similar or identical length. As shown in FIGS. 2 and 3, the tapered sections 105 may have dissimilar lengths. For example, referring to FIG. 2, the length of one of the tapered sections may be less than the length of another tapered section. Specifically, the vessel-engaging member 100 may have a working, or active, region 123 configured to perform a medical procedure and a first and second non-working, or inactive, region, 124 and 125 respectively. Each region may have a length. The working region 123 may comprise the plurality of rows 106 and a portion 126 of the tapered sections 105. The first non-working region 124 may comprise a remaining portion of a first tapered section 114. The second non-working region 125 may comprise a remaining portion of a second tapered section 115. In some embodiments, to minimize thrombogenic effects, the length of the tapered sections 105 should be minimized. Accordingly, the first non-working region 124 may have a length ranging from about 3.3 mm to about 2.6 mm and the second non-working region 125 may have a length ranging from about 5.3 mm to about 4.6 mm. In some embodiments, the difference in length between the tapered sections 114, 115 allows the connection points 113 to be aligned with one another when the vessel-engaging member 100 is collapsed (e.g., when the vessel-engaging member 100 is stowed as opposed to being deployed).

Referring to FIG. 1A, the one or more taper sections 105 may have individual cells 127 that have a different size than the individual cells 110. For example, in some embodiments, the taper sections 105 may have individual cells 127 that have a size larger than that of the individual cells 110. Each taper section 105 may taper gradually towards a connection mechanism 113, or some other connection point along the medical device that connects the vessel-engaging member 100 to the delivery wire.

In some embodiments, the tapered sections 105 allows the delivery wire to act directly on the device via the shorter tapered section 114, with the longer tapered section 115 providing stability and control. In this regard, the tapered sections 105 and complete circular design of the vessel-engaging member 100 in its deployed state may improve trackability, and may act to minimize retrieval forces, minimize the non-working length, improve pushability, and the like. For example, the vessel-engaging member 100 may have a delivery or pushability force of less than 20 N (Newton). In other examples, the delivery or pushability force may be less than 15 N, 10 N, 5 N, or 1 N. The vessel-engaging member 100 may also have a retrieval force of less than 10 N. In other examples, the retrieval force may be less than 5 N, 2 N, or 1 N. When fully expanded, the improved wall apposition enabled by the subject technology may also work to minimize thrombogenic effects. In some embodiments, a non-thrombogenic coating may further be applied to the device to further reduce the thrombogenicity of the device.

In one aspect, the one or more tapered sections 105 facilitate resheathing of the proximal portion of the vessel-engaging member 100 into the microcatheter. For example, an inner surface of the microcatheter may act upon the one or more tapered sections 105 to thereby collapse the vessel-engaging member 100 and cause it to fit within the microcatheter. The taper of the one or more tapered sections 105 thereby provide a ramping surface to cause the vessel-engaging member 100 to collapse. The device may therefore be resheathed in order to reposition or slightly adjust the position of the device within the lumen. In another aspect, the one or more tapered sections 105 may facilitate retrieval of a thrombus during a blood flow restoration procedure. For example, after the thrombus is entrained within the vessel-engaging member 100, the thrombus may be retrieved by resheathing the vessel-engaging member 100 using the one of more tapered sections 105 and the microcatheter.

In some embodiments, a width of the single and double bridges 104A, 104B disposed between the proximal row 106P and an adjacent row may be wider than other bridges of the vessel-engaging member 100. For example, referring to FIG. 2, the width of the proximal single and double bridges 112 may be 0.055 mm, whereas the width of the remaining single bridges 104A and double bridges 104B may be 0.045 mm. The increased width of the proximal single and double bridges 112 may further aid pushability because the additional width, and hence material, provides a larger load path for the longitudinal force from the pusher or delivery wire to be transmitted through the vessel-engaging member 100.

Distal Tips

In some embodiments, the vessel-engaging member 100 may also include at a distal end one or more open extending distal tips 116, 117, and 118. These distal tips 116-118 may extend from corresponding distal vertices 107B of a distal row of struts. In FIG. 1A, for example, the vessel-engaging member 100 includes a first distal tip 116, a second distal tip 117, and a third distal tip 118, each directly extending from a distal vertex of the distal row. One of the distal tips may be longer than the other or may extend out further. As shown in FIG. 1A, the second distal tip 117 is longer than the first and third distal tip, 116 and 118 respectively. The first distal tip 116 is longer than the third distal tip 118.

In some embodiments, the distal tips may be configured to be non-linear. For example, referring to FIG. 2, the first distal tip 116 and the second distal tip 117 include an angle. When the vessel-engaging member 100 is fully deployed, the angled protruding distal tips 116, 117, may fold down toward the shorter protruding tip 118 to provide a narrow and/or tapered profile at the distal end of the vessel-engaging member 100. Thus, when deployed, the vessel-engaging member 100 may be more navigable than if the distal tips were not folded.

In some embodiments, the angled protruding distal tips 116, 117, may ensnare, capture, and/or grip portions of a thrombus. Because the angled protruding distal tips 116, 117, may protrude inward slightly from the rest of the vessel-engaging member 100, the thrombus may adhere to the distal tips 116, 117. In some embodiments the distal tips 116-118 may be staggered both circumferentially and longitudinally along the distal end of the vessel-engaging member 100. The staggered placement of distal tips 116-118 may allow the thrombus to adhere to multiple distal tips, for example at different locations along the length of the thrombus.

The distal tips may include, for example, a platinum distal marker band, as discussed further below. As a marker band, the distal element may be used during an imaging process to identify a location or locations of the vessel-engaging member 100 during a medical treatment procedure.

Radiopaque Markers

Turning back to FIG. 1A, radiopaque markers may be located adjacent the proximal or distal ends 101, 102 or both, and may be located at any position along the length of the vessel-engaging member 100 between the proximal and distal ends 101, 102. In some embodiments, the markers may be located at or on the connection points 113 and/or distal tips 116-118. The markers may be attached to the vessel-engaging member 100 by techniques such as adhesives, heat fusion, interference fit, fasteners, intermediate members, coatings, or by other techniques.

In some embodiments, the markers are comprised of ultrasonic markers, MRI safe markers, or other markers. In some embodiments ultrasonic markers permit a physician to accurately determine the position of the vessel-engaging member 100 within a patient under ultrasonic visualization. Ultrasonic visualization is especially useful for visualizing the vessel-engaging member 100 during non-invasive follow-up and monitoring. Materials for an ultrasonic marker have an acoustical density sufficiently different from the medical to provide suitable visualization via ultrasonic techniques. Exemplary materials comprise polymers, metals such as tantalum, platinum, gold, tungsten and alloys of such metals, hollow glass spheres or microspheres, and other materials.

In some embodiments, MRI safe markers permit a physician to accurately determine the position of the vessel-engaging member 100 within a patient under magnetic resonance imaging. MRI visualization is especially useful for visualizing the vessel-engaging member 100 during non-invasive follow-up and monitoring. Exemplary materials for making MRI safe marker have a magnetic signature sufficiently different from the medical device to provide suitable visualization via MRI techniques. Exemplary materials comprise polymers, metals such as tantalum, platinum, gold, tungsten and alloys of such metals, non-ferrous materials, and other materials.

Connection Mechanism

In some embodiments the connection mechanism 113 may include a generally non-detachable interface or transition point between the vessel-engaging member 100 and the delivery wire 153 (shown in FIG. 4). In some embodiments the connection mechanism 113 may be integrally formed with the delivery wire 153 and/or vessel-engaging member 100. In some embodiments connection mechanisms 113 may include a releasable connection mechanism for easily releasing the vessel-engaging member 100.

Depending on the procedure and intended use of the vessel-engaging member 100, it may be advantageous to have a connection mechanism 113 that permits release of the vessel-engaging member 100. For example, the vessel-engaging member 100 may be used as an implantable member (e.g., stent) that may be released through the connection mechanism 113 at a stenosis, aneurysm, or other appropriate location in the anatomical lumen. The vessel-engaging member 100 may expand and engage a lumen wall so as to hold the lumen wall open and/or act as an occluding member. Specifically, the vessel-engaging member 100 may be used as a scaffolding to inhibit or prevent herniation or prolapse of objects (e.g., embolization coils, thrombi, etc.) out of a neck of an aneurysm. In another example, such as during a blood flow restoration procedure, it may prove difficult and/or dangerous to fully retrieve a thrombus due to a complicated vasculature or the risk of damaging a lumen wall. Leaving the vessel-engaging member 100 behind may prove to be the only option available to a surgeon or other medical personnel. In other circumstances the vessel-engaging member 100 may include drug-eluding capabilities, and/or may be coated with a particular type of drug that facilitates thrombus dissolution. It may be advantageous in such circumstances to release the vessel-engaging member 100 and allow the vessel-engaging member 100 to anchor the thrombus against the lumen wall while the thrombus is dissolved by the drug.

In some embodiments, the connection mechanism 113 may include an electrolytically severable region. For example, referring to FIGS. 4-6, the connection mechanism 113 may comprise a connection that dissolves under the influence of electrical energy when in contact with an electrolyte. The electrolytically severable region may include an exposed piece of electrolytically severable material, such as stainless steel, though other materials are also possible.

Figure 5:
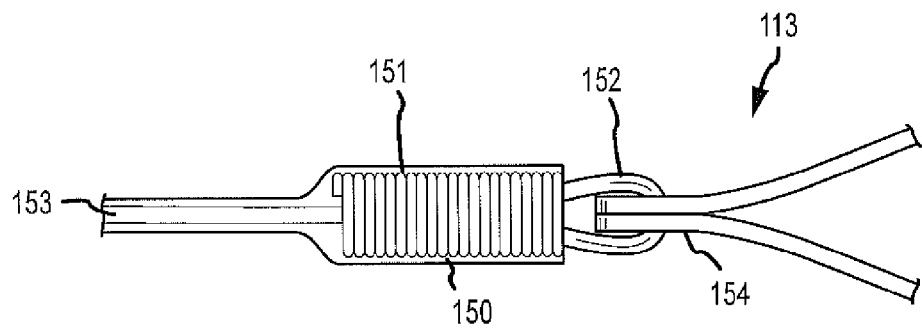
FIG. 5 depicts a top view of an electrolytically severable connection mechanism according to some embodiments of the subject technology.

As depicted in FIGS. 4 and 5, the electrolytically severable region may include a portion of the delivery wire 153. The delivery wire 153 may include an electrolytically severable region comprising a loop structure 152 that is configured to engage two tabs 154 extending from the vessel-engaging member 100. Each tab 154 includes an aperture 155 sized to receive the loop structure 152 of the delivery wire 153. In some embodiments, the entire vessel-engaging member 100, the tab 154, or the aperture 155, may be coated be with an insulating coating, such as parylene (though other types of coating material are also possible), to electrically insulate the vessel-engaging member 100 from the electrical energy. In some embodiments, the vessel-engaging member 100 may be formed from a material that is not prone to electrolytic disintegration, such as NITINOL®. A portion of the delivery wire 153 may be isolated to prevent electrolytic disintegration of said portion. For example, a Polytetrafluoroethylene (PTFE) shrink tube 150 may be disposed over the delivery wire 153 to prevent electrolytic disintegration of the delivery wire 153 at the shielded portion. Specifically, the shrink tube 150 prevents the electrolyte (e.g., blood) from contacting the shielded portion. In some embodiments, the loop structure 152 may be formed by bending the delivery wire 153 and securing the bent portion onto the delivery wire 153 with a radiopaque marker 151. The radiopaque marker 151 may be attached to the delivery wire 153 by techniques such as adhesives, heat fusion, interference fit, fasteners, intermediate members, coatings, or by other techniques.

Figure 6:
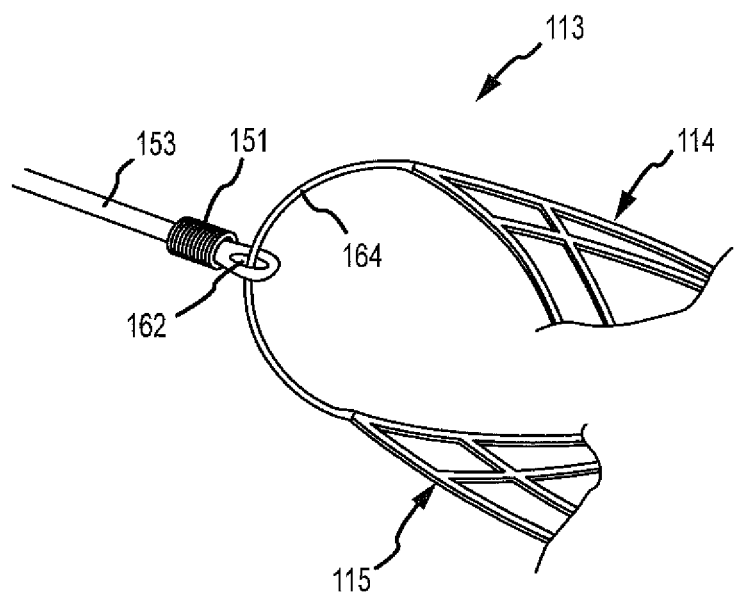
FIG. 6 depicts a perspective view of an electrolytically severable connection mechanism according to some embodiments of the subject technology.

Referring to FIG. 6, the delivery wire 153 may include a loop structure 162 that is configured to engage an electrolytically severable region 164 of the vessel-engaging member 100. The severable region 164 may comprise a member extending between the first and second tapered sections, 114 and 115 respectively.

Overall, the structure of connection mechanism 113 may be configured such that the vessel-engaging member 100 releases at a predetermined point. For example, the vessel-engaging member 100 may generally be isolated from electric current, such that during detachment of the vessel-engaging member 100, only the electrolytically severable region disintegrates in blood, and the vessel-engaging member 100 separates from the delivery wire 153 cleanly at the electrolytically severable region, and is released into the anatomical lumen.

In some embodiments, the connection mechanism 113 may include a mechanical connection. Referring to FIGS.

Figure 7:
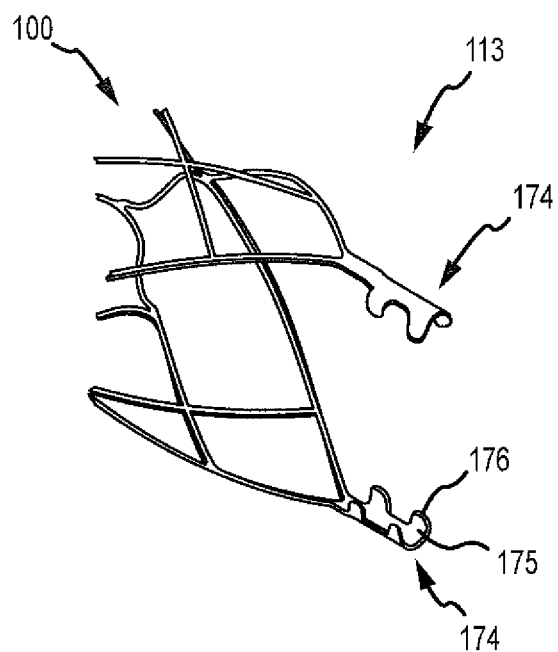
FIG. 7 depicts a perspective view of a mechanically severable connection mechanism according to some embodiments of the subject technology.
Figure 8:
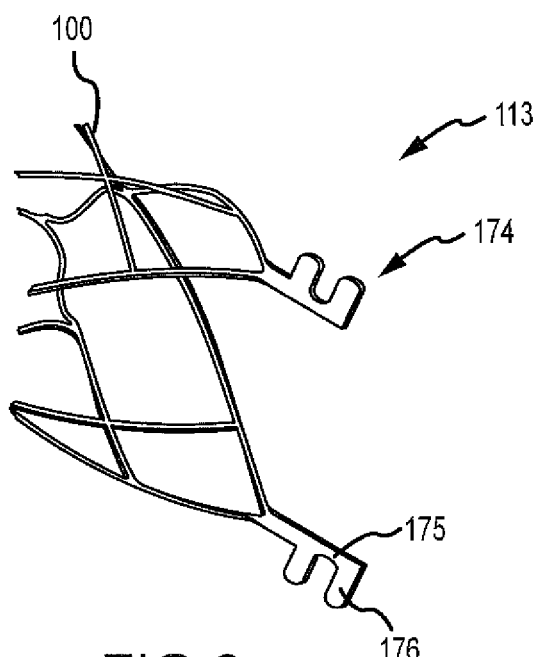
FIG. 8 depicts a mechanically severable connection mechanism according to some embodiments of the subject technology.

7-10, the connection mechanism 113 may comprise two interlocking fingers 174 that are configured to couple the delivery wire 153. Each interlocking finger 174 may comprise a tab 175 with fingers 176 extending therefrom, that are disposed on a proximal end of the vessel-engaging member 100. As depicted in FIG. 7, the fingers 176 may extend from opposite edges of the tab 175. Alternatively, as depicted in FIG. 8, the fingers 176 may extend from a common edge of the tab 175. In either case, the tab 175 and fingers 176 are configured to have a curvature for facilitating coupling with the delivery wire 153.

Figure 9:
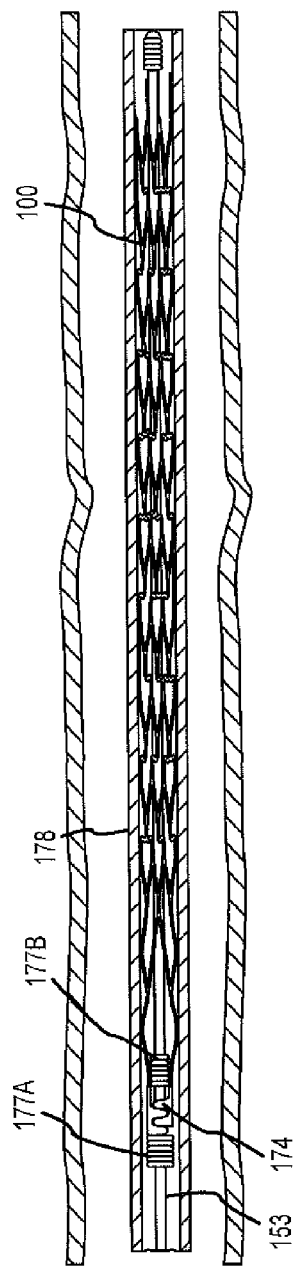
FIG. 9 depicts a partial cross section of a compressed medical device having a mechanically severable connection mechanism according to some embodiments of the subject technology.
Figure 10:
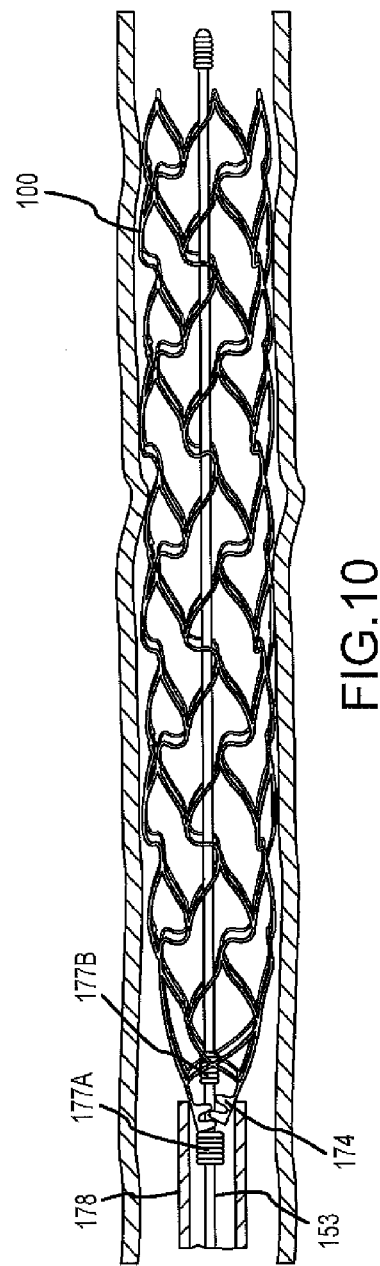
FIG. 10 depicts a partial cross section of an expanded medical device having a mechanically severable connection mechanism according to some embodiments of the subject technology.

Referring to FIGS. 9 and 10, the interlocking fingers 174 couple the delivery wire 153 at a coupling area of the delivery wire 153 that is between a first and second bumper or radiopaque marker, 177A and 177B respectively. The first and second radiopaque markers, 177A and 177B respectively, prevent the interlocking fingers from sliding beyond the coupling area and thereby act as stops for the interlocking fingers 174. The interlocking fingers 174 are forced onto the coupling area of the delivery wire by an outer sheath or microcatheter 178 that surrounds the interlocking fingers 174.

Referring to FIG. 10, proximal movement of the microcatheter 178 or distal movement of the delivery wire 153, with the vessel-engaging member 100 coupled thereto, releases the interlocking fingers 174 from the delivery wire 153 via expansion of the vessel-engaging member 100. Accordingly, upon expansion of the proximal end 101 of the vessel-engaging member 100, the interlocking fingers 174 release the delivery wire 153, thereby releasing the vessel-engaging member 100 from the delivery wire 153.

Figure 13:
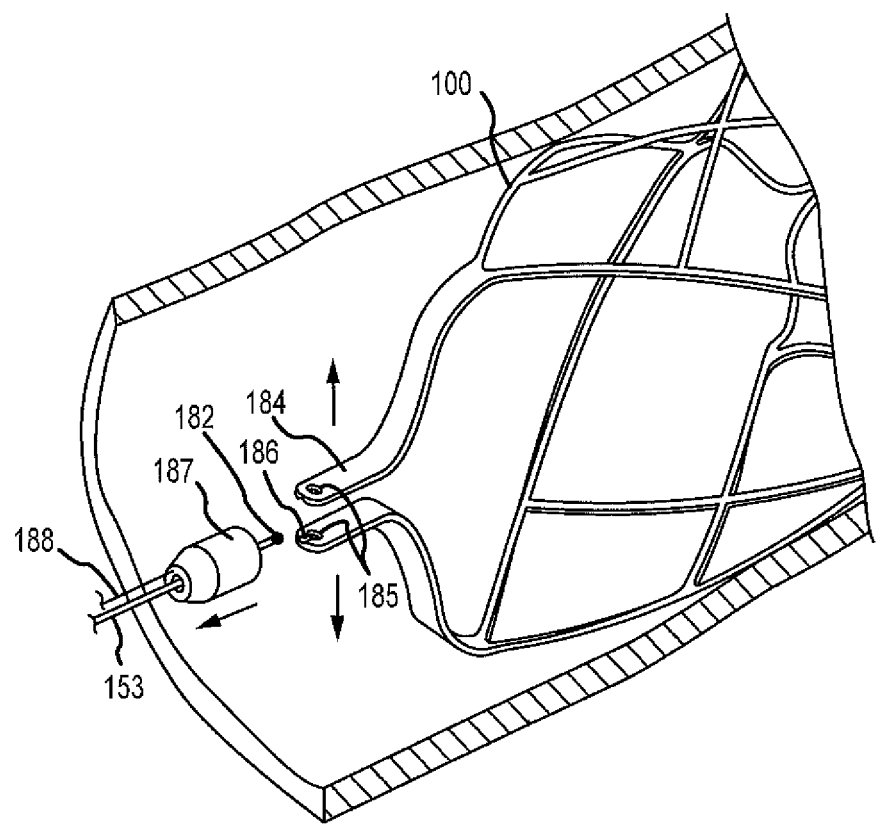
FIG. 13 depicts a perspective view a mechanically severable connection mechanism according to some embodiments of the subject technology.

Referring to FIGS. 11-13, the connection mechanism 113 may comprise a ball 182, located at a distal end of the delivery wire 153, and two paddles 184 configured to couple the ball 182. Each paddle 184 may comprise an aperture 185 configured to couple to an outer surface of the ball 182. Each paddle 184 may be configured with a channel 186 to provide clearance for the delivery wire 153, so as to prevent an interference between the paddle 184 and the delivery wire 153 when the paddles 184 are coupled to the ball 182. Each paddle is disposed on a proximal end 101 of the vessel-engaging member 100.

As depicted in FIGS. 11-13, the paddles 184 couple the delivery wire 153 at the ball 182. The paddles 184 may be forced onto the ball 182 by a retractable sleeve 187 that surrounds the paddles 184 and the ball 182. The sleeve 187 may be comprised of platinum, though other materials are also possible. Proximal movement of the sleeve 187, via a wire 188 or other mechanical means, releases the paddles 184 from the delivery wire 153 via expansion of the vessel-engaging member 100. Accordingly, upon expansion of the proximal end 101 of the vessel-engaging member 100, the paddles 184 release the ball 182 of the delivery wire 153, thereby releasing the vessel-engaging member 100 from the delivery wire 153.

Figure 14:
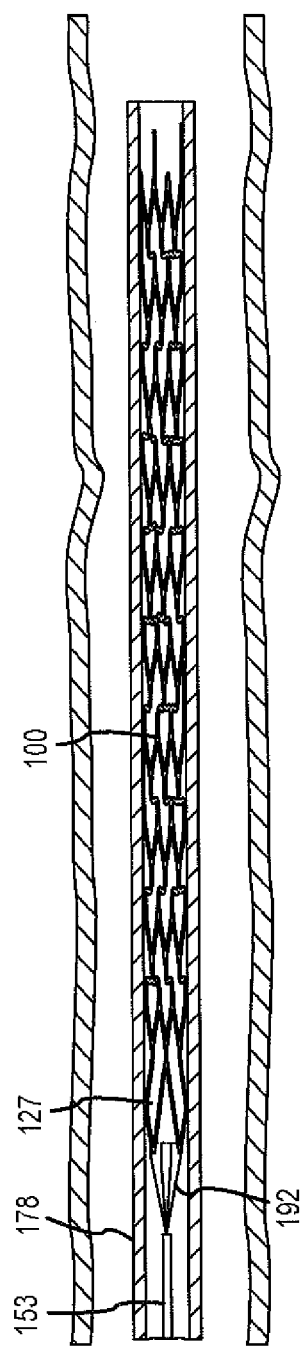
FIG. 14 depicts a partial cross section of a compressed medical device having a mechanically severable connection mechanism according to some embodiments of the subject technology.
Figure 15:
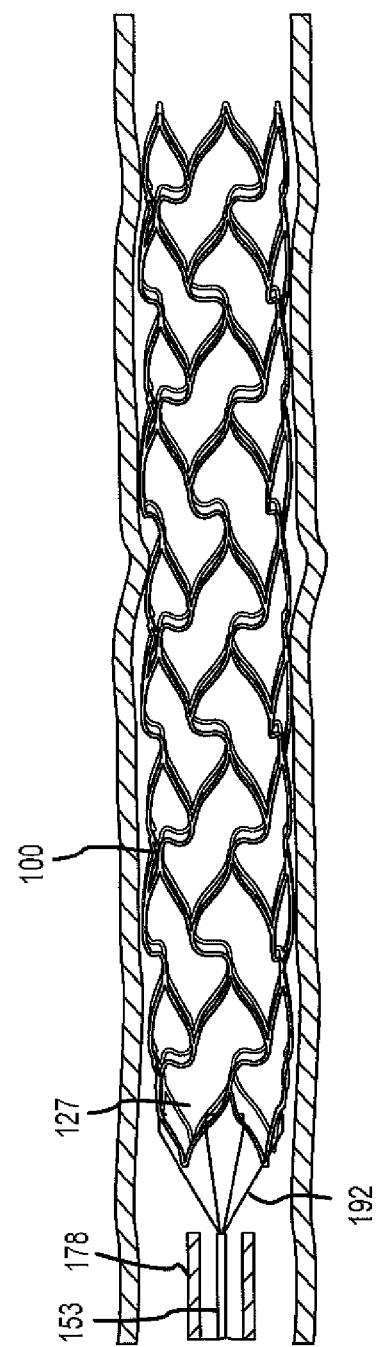
FIG. 15 depicts a partial cross section of an expanded medical device having a mechanically severable connection mechanism according to some embodiments of the subject technology.

Referring to FIGS. 14-15, the connection mechanism 113 may comprise a plurality of grasping jaws 192 that are attached to a distal end of the delivery wire 153. The grasping jaws 192 may, for example, comprise an Alligator Retrieving Device ("ARD") as manufactured by Covidien®. The grasping jaws 192 may be configured to engage the proximal end 101 of the vessel-engaging member 100. As depicted in FIG. 15, the grasping jaws 192 may engage the open cells 127 adjacent the proximal end 101 of the vessel-engaging member 100. The grasping jaws 192 may be manipulated to open and close by a retractable sleeve or microcatheter 178 that surrounds the grasping jaws 192. Proximal movement of the microcatheter or distal movement of the delivery wire 153 releases the grasping jaws 192 from the vessel-engaging member 100.

The grasping jaws 192 may be configured to release the vessel-engaging member 100 by allowing the tips of each grasping jaw to deflect and release the vessel-engaging member 100 upon proximal movement of the delivery wire 153 and the grasping jaws 192. Once expanded within the anatomical lumen, friction between the outer surface of the vessel-engaging member 100 and the anatomical lumen, prevents the vessel-engaging member 100 from moving proximally with the delivery wire 153 and the grasping jaws 192.

Referring to FIGS. 16-17, the connection mechanism 113 may comprise an inner sheath 194 that is configured to surround the vessel-engaging member 100 and maintain the vessel-engaging member 100 in a compressed configuration. The inner sheath 194 has an outer diameter that is less than the inner diameter of the microcatheter 178. In some embodiments, the inner sheath 194 extends along the entire length of the vessel-engaging member 100. As depicted in FIG. 17, proximal movement of the inner sheath 194 or distal movement of the delivery wire 153, allows the vessel-engaging member 100 to expand in the anatomical lumen. To release the vessel-engaging member 100, the inner sheath 194 is moved proximal of the proximal end 101 of the vessel-engaging member 100, thereby allowing the vessel-engaging member to expand and be free from the inner sheath 194. To prevent the vessel-engaging member from shifting during proximal retraction of the inner sheath 194, one or more bumpers 195 may be disposed along the delivery wire 153 to engage the proximal end 101 and/or the distal end 102 of the vessel-engaging member 100 when the vessel-engaging member 100 is in the compressed configuration.

In some embodiments, one or more radiopaque markers may be disposed along the delivery wire 153. For example, referring to FIGS. 16-17, a radiopaque marker 196 may be disposed at the distal end of the delivery wire 153. In other aspects, a radiopaque marker 197 may be disposed proximal of the vessel-engaging member 100.

The strut 103, single bridge 104A, and double bridge 104B configuration of the vessel-engaging member 100 may be formed, for example, by laser cutting a pre-formed tube or sheet, by interconnecting a multitude of filaments by laser welding, or by other suitable methods such as electrochemical etching, grinding, piercing, electroforming, or other means. In one arrangement, the vessel-engaging member 100 may be comprised of metal, polymer, ceramic, permanent enduring materials, and may comprise either of or both of non-bioabsorbable and bioabsorbable materials. Exemplary materials include, but are not limited to, NITINOL®, stainless steel, cobalt chromium alloys, Elgiloy, magnesium alloys, polylactic acid, poly glycolic acid, poly ester amide (PEA), poly ester urethane (PEU), amino acid based bio-analogous polymers, tungsten, tantalum, platinum, polymers, bio-polymers, ceramics, bio-ceramics, or metallic glasses. Part or all of the medical device may elute over time substances such as drugs, biologics, gene therapies, antithrombotics, coagulants, anti-inflammatory drugs, immunomodulator drugs, anti-proliferatives, migration inhibitors, extracellular matrix modulators, healing promoters, re-endothelialization promoters, or other materials. In some embodiments, the vessel-engaging member 100 may be formed from materials having shape memory properties. In some embodiments, the vessel-engaging member 100 may be finished by processes to remove slag. In some embodiments, the vessel-engaging member 100 may be subjected to a tempering treatment at temperatures customarily applied to the material so that the impressed structure is permanently established.

The vessel-engaging member 100 may have various lengths and diameters. For example, the vessel-engaging member 100 may have specific cross-sectional diameters, the diameters being measured when the vessel-engaging member 100 is fully free to expand, ranging from about 2 mm to about 6 mm. If the vessel-engaging member 100 has a diameter between 3 mm and 4 mm, it may be used in a size 18 microcatheters (i.e., microcatheters with an inner diameter of approximately 0.21 inch). If the vessel-engaging member 100 has a diameter between 5 mm and 6 mm, it may be used in a size 27 microcatheters (i.e., microcatheters with an inner diameter of approximately 0.027 inch). However, other suitable cross-sectional diameters may be used without deviating from the scope of the subject technology. In some embodiments, the vessel-engaging member may have lengths, measured proximally to distally along the longitudinal axis 109, ranging from 15 mm to 40 mm, though other ranges and sizes are also possible.

Skilled artisans may implement the described functionality in varying ways for each particular application. Various components and blocks may be arranged differently (for example, arranged in a different order, or partitioned in a different way) all without departing from the scope of the subject technology. It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (for example, his) include the feminine and neuter gender (for example, her and its) and vice versa. Headings and subheadings, if any, are used for convenience only and do not limit the invention.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "aspect" does not imply that such aspect is essential to the subject technology or that such aspect applies to all configurations of the subject technology. A disclosure relating to an aspect may apply to all aspects, or one or more aspects. An aspect may provide one or more examples. A phrase such as an "aspect" may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A medical device, comprising:
   a delivery wire having a proximal end and a distal end; and
   a vessel-engaging member attached to the distal end of the delivery wire, the vessel-engaging member comprising:
   a plurality of rows, each row having a plurality of struts arranged in an alternating pattern such that for each row, a first set of vertices is positioned on a proximal side, and a second set of vertices is positioned on a distal side;
   a plurality of single bridges positioned between pairs of adjacent rows, each of the single bridges connecting a single vertex of a first row of each pair of adjacent rows with a single vertex of a second row of each pair of adjacent rows; and
   a plurality of double bridges positioned between the pairs of adjacent rows, each of the double bridges connecting a single vertex of the first row of each pair of adjacent rows with two vertices of the second row of each pair of adjacent rows, the two vertices of the second row being adjacent to each other, wherein each of the plurality of double bridges is arranged generally along a line progressing laterally at an angle with respect to a longitudinal axis of the member.

2. The medical device of claim 1, wherein the first set of vertices are laterally offset from the second set of vertices.

3. The medical device of claim 1, wherein the plurality of single bridges positioned between a first row and an adjacent second row extend from the second set of vertices of the first row, downward to the first set of vertices of the second row, and wherein the plurality of single bridges positioned between the second row and an adjacent third row extends from the second set of vertices of the second row, upward to the first set of vertices of the third row.

4. The medical device of claim 1, wherein the plurality of double bridges are more rigid than the plurality of single bridges and thereby communicate a larger proportion of a longitudinal force than the plurality of single bridges.

5. The medical device of claim 1, wherein the plurality of single bridges comprises undulating members.

6. The medical device of claim 1, wherein the plurality of double bridges comprises undulating members.

7. The medical device of claim 1, wherein the single bridges positioned between a first row and an adjacent second row alternate laterally with the double bridges positioned between said adjacent rows.

8. The medical device of claim 7, wherein the alternating single and double bridges form a laterally-repeating pattern of two adjacent single bridges and one double bridge adjacent to one of the two adjacent single bridges.

9. The medical device of claim 8, wherein the single and double bridges positioned between the second row and an adjacent third row form the same laterally-repeating pattern as between the first row and the second row, wherein the double bridges between the second and third row are offset laterally from the double bridges between the first and second row.

10. The medical device of claim 8, wherein:
the single and double bridges positioned between the second row and an adjacent third row form the same laterally-repeating pattern as between the first row and the second row;
the single and double bridges positioned between the third row and an adjacent fourth row form the same laterally-repeating pattern as between the first row and the second row, and as between the second row and the third row;
the double bridges between the second row and the third row are aligned laterally with the double bridges between the first row and the second row; and
the double bridges between the third row and the fourth row are offset laterally from the double bridges between the first row and the second row, and from the double bridges between the second row and the third row.

11. The medical device of claim 10, wherein the pattern thus formed by the double bridges between the first row and the second row, the double bridges between the second row and the third row, and the double bridges between the third row and the fourth row, consisting of two longitudinally adjacent, laterally aligned sets of double bridges followed by one set of double bridges longitudinally adjacent to one of the two aligned sets and laterally offset therefrom, repeats along the length of the medical device.

12. The medical device of claim 10, wherein the double bridges between the third row and the fourth row are offset laterally from the double bridges between the first row and the second row, and from the double bridges between the second row and the third row, to the next lateral inter-vertex position on the distal vertices of the third row.

13. The medical device of claim 1, wherein the plurality of single bridges and the plurality of double bridges positioned between a first row and an adjacent second row are laterally offset from the plurality of single bridges and the plurality of double bridges positioned between the second row and an adjacent third row.

14. The medical device of claim 1, wherein an adjacent plurality of double bridges is positioned between the second row and a third row, the adjacent plurality of double bridges being longitudinally spaced from the plurality of double bridges.

15. The medical device of claim 1, further comprising first and second tapered sections, each of the tapered sections projecting from a proximal row and tapering in a direction from the proximal row toward the delivery wire.

16. The medical device of claim 15, wherein the first tapered section comprises a first and second connecting member with distal ends connected to the proximal row and proximal ends connected to the first tapered section.

17. The medical device of claim 16, wherein the first and second connecting members intersect.

18. The medical device of claim 15, wherein the first tapered section is connected to the proximal row at a middle vertex and a first strut endpoint, and the second tapered section is connected to the proximal row at the middle vertex and a second strut endpoint.

19. The medical device of claim 1, wherein each vertex of the second set of vertices in each first row of each pair of adjacent rows is attached directly to only one bridge, of the plurality of single bridges or the plurality of double bridges.

20. A medical device for insertion into a vessel, comprising:
a frame comprising a plurality of rows, each row having a plurality of struts arranged in an alternating pattern such that for each row, a first set of vertices is positioned on a proximal side, and a second set of vertices is positioned on a distal side offset from the first set of vertices;
a plurality of single bridges positioned between adjacent rows, each of the bridges connecting a single vertex of the second set of vertices of a first row with a single vertex of the first set of vertices of a second row; and
a plurality of double bridges positioned between adjacent rows, each of the double bridges connecting a single vertex of the first row with two vertices of the second row, the two vertices of the second row being adjacent to each other, wherein each of the plurality of double bridges is arranged generally along a line progressing laterally at an angle with respect to a longitudinal axis of the member.

21. The medical device of claim 20, wherein the first set of vertices are laterally offset from the second set of vertices.

22. The medical device of claim 20, wherein the plurality of single bridges positioned between a first row and an adjacent second row extend from the second set of vertices of the first row, downward to the first set of vertices of the second row, and wherein the plurality of single bridges positioned between the second row and an adjacent third row extends from the second set of vertices of the second row, upward to the first set of vertices of the third row.

23. The medical device of claim 20, wherein the plurality of double bridges are more rigid than the plurality of single bridges and thereby communicate a larger proportion of a longitudinal force than the plurality of single bridges.

24. The medical device of claim 20, wherein the plurality of single bridges comprises undulating members.

25. The medical device of claim 20, wherein the plurality of double bridges comprises undulating members.

26. The medical device of claim 20, wherein the single bridges positioned between a first row and an adjacent second row alternate laterally with the double bridges positioned between said adjacent rows.

27. The medical device of claim 26, wherein the alternating single and double bridges form a laterally-repeating pattern of two adjacent single bridges and one double bridge adjacent to one of the two adjacent single bridges.

28. The medical device of claim 27, wherein the single and double bridges positioned between the second row and an adjacent third row form the same laterally-repeating pattern as between the first row and the second row, wherein the double bridges between the second and third row are offset laterally from the double bridges between the first and second row.

29. The medical device of claim 27, wherein:
the single and double bridges positioned between the second row and an adjacent third row form the same laterally-repeating pattern as between the first row and the second row;

the single and double bridges positioned between the third row and an adjacent fourth row form the same laterally-repeating pattern as between the first row and the second row, and as between the second row and the third row;

the double bridges between the second row and the third row are aligned laterally with the double bridges between the first row and the second row; and the double bridges between the third row and the fourth row are offset laterally from the double bridges between the first row and the second row, and from the double bridges between the second row and the third row.

30. The medical device of claim 29, wherein the pattern thus formed by the double bridges between the first row and the second row, the double bridges between the second row and the third row, and the double bridges between the third row and the fourth row, consisting of two longitudinally adjacent, laterally aligned sets of double bridges followed by one set of double bridges longitudinally adjacent to one of the two aligned sets and laterally offset therefrom, repeats along the length of the medical device.

31. The medical device of claim 29, wherein the double bridges between the third row and the fourth row are offset laterally from the double bridges between the first row and the second row, and from the double bridges between the second row and the third row, to the next lateral inter-vertex position on the distal vertices of the third row.

32. The medical device of claim 20, wherein the plurality of single bridges and the plurality of double bridges positioned between a first row and an adjacent second row are laterally offset from the plurality of single bridges and the plurality of double bridges positioned between the second row and an adjacent third row.

33. The medical device of claim 20, wherein an adjacent plurality of double bridges is positioned between the second row and a third row, the adjacent plurality of double bridges being longitudinally spaced from the plurality of double bridges.

34. The medical device of claim 20, further comprising first and second tapered sections, each of the tapered sections projecting from a proximal row and tapering in a direction from the proximal row toward the delivery wire.

35. The medical device of claim 34, wherein the first tapered section comprises a first and second connecting member with distal ends connected to the proximal row and proximal ends connected to the first tapered section.

36. The medical device of claim 35, wherein the first and second connecting members intersect.

37. The medical device of claim 34, wherein the first tapered section is connected to the proximal row at a middle vertex and a first strut endpoint, and the second tapered section is connected to the proximal row at the middle vertex and a second strut endpoint.

38. The medical device of claim 20, wherein each vertex of the second set of vertices in each first row is attached directly to only one bridge, of the plurality of single bridges or the plurality of double bridges.

* * * * *